United States Patent [19]

Buchalter

[11] Patent Number: 5,873,367
[45] Date of Patent: Feb. 23, 1999

[54] METHOD FOR BREAST TISSUE EXAMINATION

[75] Inventor: Gilbert Buchalter, Millburn, N.J.

[73] Assignee: Millburn Marketing Associates, Millburn, N.J.

[21] Appl. No.: 800,846

[22] Filed: Feb. 14, 1997

Related U.S. Application Data

[60] Provisional application No. 60/014,385 Mar. 28, 1996.
[51] Int. Cl. $^6$ .................................................. A61B 19/00
[52] U.S. Cl. ............................................ 128/898; 600/300
[58] Field of Search .................................... 128/898, 897; 623/66; 600/300, 437, 549, 445, 448; 604/346

[56] References Cited

U.S. PATENT DOCUMENTS

| | | |
|---|---|---|
| 3,989,050 | 11/1976 | Buchalter . |
| 4,002,221 | 1/1977 | Buchalter . |
| 4,657,021 | 4/1987 | Perry et al. ........................ 128/897 X |
| 4,873,982 | 10/1989 | Morrison ................................ 600/300 |
| 5,474,064 | 12/1995 | Rohrberg ............................ 128/915 X |
| 5,572,995 | 11/1996 | Rohrberg ................................ 600/300 |

OTHER PUBLICATIONS

*Breast Self–Examination—The Key To Breast Health* No Date or Author.
*Why Do The Breast Self–Exam?* No Date or Author.
*Breast Self–Examination* No Date or Author.
*10 Easy Steps For Monthly Breast Exams,* Saint Barnabas Outpatient Centers No Date or Author.
New "The Other Breast Problems Every Woman Must Recognize" Ladies Home Journal, V. 108, N. 3, p. 84(4), Mar. 1991.
Berger et al. "How to do a Breast Self–Examination" Cosmopolitan, pp. 174 and 178, Oct. 1994.

*Primary Examiner*—Mickey Yu
*Assistant Examiner*—Kelly O'Hara
*Attorney, Agent, or Firm*—Lerner, David, Littenberg, Krumholz & Mentlik

[57] ABSTRACT

A method for examining the breast tissue of an individual for the presence of lumps or a change in texture, which method includes the steps of:

applying to the skin of the individual in the area of the breast tissue while the skin is substantially dry an amount of an aqueous emulsion or gel composition effective to lubricate the skin; and feeling the skin of the individual by hand for a lump or thickening in the underlying tissue;

whereby the lubricating effect of the emulsion or gel composition increases the tactile sensation of the texture of the breast tissue.

11 Claims, No Drawings

METHOD FOR BREAST TISSUE EXAMINATION

The present application claims benefit of U.S. Provisional Application Ser. No. 60/014,385, filed Mar. 28, 1996, now abandoned.

BACKGROUND OF THE INVENTION

The present invention relates to a method for examining breast tissue for the presence of lumps or a change in texture, and in particular to a method in which an aqueous emulsion or gel composition is applied to the skin of an individual in the area of the breast tissue while the skin is substantially dry in an amount effective to lubricate the skin, so as to increase the tactile sensation of the texture of the underlying breast tissue.

Monthly examination of breast tissue is a valuable tool in the early detection of breast disease and in particular breast cancer. Breast cancer is most easily treated and cured when it is found early. Self-examination is a convenient method for regular breast tissue examination without having to schedule an appointment with a health professional. Monthly self-examination also permits the individual to become familiar with the texture of their breast tissue, to better ensure the early detection of a lump or thickening.

Health professionals recommend a self-examination performed in a reclining position, for example with the right arm extended out, with the elbow at a 90 degree angle. The left hand is then used to feel the tissue underneath the skin of the right breast for a lump or thickening. The technique is then repeated with the left arm extended outward and the right hand used to feel the tissue of the left breast for a lump or thickening.

Health professionals also recommend additional self-examination in the shower or bath. Soapiness of the hands and the skin in the area of the breast tissue increases the tactile sensation of the texture of the breast tissue, making it easier to detect a change in the texture of the tissue. The examination, however, is ideally performed in the aforementioned reclining position, which flattens the breast and makes it easier to examine. While this is not convenient in the shower, a standing examination in the shower is no substitute for the examination in the reclining position recommended by health professionals, in fact both reclining and standing are recommended for a thorough examination.

While a soap solution could be used during a breast self-examination outside the shower when the skin in the area of the breast is substantially dry and the individual can assume a reclining position, the soap solution dries rapidly on the dry skin, forming a film that resists rather than lubricates the movement of the hands over the skin, thereby interfering with the tactile sensation of the breast tissue texture. After the examination, the soap film must be washed away. There remains a need for a means by which tactile sensation may be increased during breast self-examination when the skin in the area of the breast tissue is substantially dry, so as to facilitate individual self-examination while in the reclining position as recommended by health professionals.

SUMMARY OF THE INVENTION

This need is met by the present invention. It has now been discovered that an aqueous emulsion or gel composition applied to substantially dry skin before a breast examination lubricates the skin to increase the tactile sensation of the texture of breast tissue. The film layer formed by the emulsion or gel composition not only has a greater lubricating effect than a soap solution film, the emulsion or gel composition dries much more slowly than a soap solution film, permitting the examination of the entire breast with a single application.

Therefore, according to one embodiment of the present invention, a method is provided for examining the breast tissue of an individual for the presence of lumps or a change in texture, which method includes the steps of:

applying to the skin of the individual in the area of the breast tissue while the skin is substantially dry an amount of an aqueous emulsion or gel composition effective to lubricate the skin; and feeling the skin of the individual by hand for a lump or thickening in the underlying tissue;

whereby the lubricating effect of the emulsion or gel increases the tactile sensation of the texture of the breast tissue.

The examination may be performed by a health professional, or may be a self-examination by the individual. The examination is preferably performed with the individual in a reclining position.

Without being bound by any particular theory, it is believed that emulsion and gel compositions, by being colloidal systems, contain entrapped water which contributes to the slow drying and superior lubricating effect of the emulsion or gel. This also gives the emulsion or gel composition an emollient effect, so that, unlike soap solutions, it is not necessary to remove the emulsion or gel composition from the skin following the examination. Even if removal is desired, the emulsion or gel composition is easily removed with a dry or damp cloth or towel. Other features of the present invention will be pointed out in the following description and claims, which disclose the principals of the invention and the best modes which are presently contemplated for carrying them out.

DETAILED DESCRIPTION OF THE PREFERRED EMBODIMENT

The method of the present invention applies to the skin of an individual in the area of the breast tissue to be examined an amount of an aqueous emulsion or gel composition effective to lubricate the skin. Between about 1 and about 30 mL of the emulsion or gel composition should be applied to the skin, and preferably between about 5 and about 10 ML.

The emulsion or gel composition should leave a greaseless and non-staining film residue. For this reason, the materials are defined as being aqueous, although the emulsion composition may be a water-in-oil or oil-in-water emulsion, so long as the composition leaves a greaseless and non-staining residue.

For purposes of the present invention, the terms "gel" and "emulsion" are given their commonly understood meaning in colloid chemistry. That is, emulsion compositions are dispersions of one liquid in another, typically one phase being aqueous and the other being an oil. Either the oil phase or the aqueous phase may be the disperse phase. Examples of emulsion compositions suitable for use with the present invention include lotions and creams for dry skin, massage and cleansing.

Aqueous gel compositions are preferred over aqueous emulsions. A gel composition is a colloidal disperse system in which is contained a dispersed component and a dispersion medium, both extending continuously throughout the system. Examples of gel compositions suitable for use with the present invention include the gel compositions described in U.S. Pat. Nos. 3,989,050 and 4,002,221, the disclosures of which are incorporated herein by reference. The patents describe ultrasonic conductivity gel compositions marketed by Pharmaceutical Innovations, Inc. of Newark, N.J., under the trade names ULTRAPHONIC conductivity gel, LECTRON II conductivity gel, ULTRAPHONIC SG scanning gel and GAMMA massage and ultrasound gel. The repackaging of such products for consumer use is contemplated.

Preferred gel formulations are based on alkali metal salts of long chain ionic organic polymers, including, for example, copolymers of methyl vinyl ethers and maleic acid, carboxy polymethylene polymers sold by B.F. Goodrich Chemical Company under the trade name CARBOPOL, sodium alginate, gum tragacanth, locust bean gum, polyethylene oxide, sodium carboxymethyl cellulose, guar gum, methyl cellulose, and the like. Carboxypolymethylene polymers are preferred.

The gel formulation may also include a second cellulose-based polymeric thickener such as hydroxy methyl cellulose, hydroxy ethyl cellulose, methyl cellulose, hydroxypropyl cellulose, and the like. The second polymeric thickener is not present in the form of a metal salt, but has at least one primary hydroxy group attached to each repeating unit in the cellulose backbone. The cellulose-based polymer should have a one weight percent solution Brookfield viscosity (20 rpm at 25° C.) between about 100 and 10,000 cps.

The two polymers function as the dispersed component and are typically dispersed in an aqueous dispersion medium.

The ionic organic polymer should be present in a concentration between about $1/20$ of one weight percent and about ten weight percent, and preferably between about $1/4$ of one weight percent and five weight percent. The polymer should have molecular weight between about 30,000 and about 2,000,000 daltons and preferably between about 60,000 and about 500,000 daltons. Solution concentrations of the polymer of one weight percent should have a Brookfield viscosity at 20 rpm at 25° C. between about 1,000 and about 100,000 cps., and preferably between about 15,000 and about 90,000 cps. Carboxypolymethylene polymers preferred for use in the present invention include the 934, 940 and 941 members of the CARBOPOL series.

The cellulose-based second polymeric thickener should be of the highest molecular weight possible without being insoluble in the aqueous glycol dispersion medium. The concentration of the second polymeric thickener should range between about $1/1,000$ of one percent to about three percent by weight, and preferably between about $1/100$ of one percent to about one percent by weight.

The gel composition dispersion medium may optionally include a glycol content up to about 25 percent by weight and preferably between about 14 and about 20 percent by weight. When present, alkylene glycols having from 2 to 10 carbon atoms are suitable for use with the present invention, with alkylene glycols containing from 2 to 5 carbon atoms being preferred. Propylene glycol is the preferred glycol.

The pH of the gel should range between about 3.5 and about 11.5, and preferably between about 5 and about 9.5. Most preferably, the pH should be adjusted to be as close to the pH of the human skin as possible.

Particularly preferred gel compositions contain from about $1/20$ of one weight percent to about ten weight percent of a carboxypolymethylene polymer having a Brookfield viscosity at 25° C. between about 1,000 and 100,000 cps. at 20 rpm at a one weight percent concentration in water, which has been neutralized with an alkali metal hydroxide; from about $1/1,000$ of one percent to about three weight percent of hydroxyethyl cellulose having a one weight percent solution Brookfield viscosity at 25° C. between about 100 and about 10,000 cps. at 200 rpm; and from about 10.5 to about 25 weight percent of propylene glycol; with the balance being essentially water. Up to about 5 weight percent of weak organic acids and alkali metal salts thereof may be present to buffer the pH of the gel.

Most preferably, the gel formulation will contain between bout $1/10$ of one weight percent and about three weight percent of the carboxypolymethylene polymer, between about $1/10$ of one weight percent and about three weight percent of hydroxyethyl cellulose, between about 14 weight percent and about 22 weight percent of propylene glycol, with the balance essentially water. A specific formulation that may be prepared for use with the method of the present invention contains about $1/2$ of one weight percent of carboxypolymethylene polymer, about $1/4$ of one weight percent of hydroxyethyl cellulose, and about 18 weight percent propylene glycol, with the balance essentially water containing about 40 weight percent of sodium hydroxide based upon the amount of carboxypolymethylene polymer present.

The method of the present invention may be performed by applying the emulsion or gel composition directly to the skin. Alternatively, the emulsion or gel composition may be applied to the skin by hand while feeling the skin in the area of the breast tissue for a lump or thickening in the underlying tissue.

The method of the present invention may be performed on an individual by a health professional. Alternatively, the method may be performed as a self-examination by the individual. The method is preferably performed while the individual is in a reclining position.

Otherwise, the examination is performed as a conventional breast examination or self-examination. The examination of each breast typically can be completed with a single application of emulsion or gel composition. Upon completion, a greaseless and non-staining residue remains that may be left on the skin to take advantage of its emollient properties or wiped clean with a dry or damp cloth or towel.

The use of the emulsion or gel composition increases the tactile sensation of breast tissue texture by facilitating the sliding movement of the hands and fingers on the skin in the area of the breast tissue. The method of the present invention employing emulsion and gel compositions as lubricants for substantially dry skin in breast tissue examination procedures represents an improvement in breast tissue examination methods.

As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A method for conducting a breast self examination by palpating breast tissue with fingers comprising the steps of:
   applying directly to a surface of a breast while said surface is substantially dry an amount of an aqueous emulsion or gel composition effective to lubricate said surface; and
   feeling the lubricated surface by palpating a breast for a lump or thickening in underlying tissue;
   wherein said aqueous emulsion or gel composition is in an aqueous dispersion medium from about $1/20$ of one weight percent to about ten weight percent of a long chain water-soluble ionic polymeric thickener having a Brookfield viscosity (20 rpm at 25° C.) of between about 1,000 and about 100,000 cps. at a one weight percent concentration in water, which has been neutralized with an alkali metal hydroxide; and from about 1/1,000 of one weight percent to about three weight percent of a cellulosic backbone thickener having no metallic ion constituent which has at least one primary hydroxy group attached to each repeating unit in the cellulose backbone and having a one weight percent solution viscosity (Brookfield at 20 rpm and at 25° C.) between about 100 and about 10,000 cps; and wherein said gel composition has a pH between about 3.5 and about 11.5; and whereby the lubricating effect of said emulsion or gel composition increases the tactile sensation of the texture of the breast tissue.

2. The method of claim 1, wherein said method of applying said emulsion or gel to said skin comprises applying said emulsion or gel composition directly to said skin.

3. The method of claim 1, wherein said method of applying said emulsion or gel composition to said skin comprises applying said composition to said skin with said hand while feeling said skin for said lump or thickening in said underlying tissue.

4. The method of claim 1, wherein said breast tissue is examined by a health professional.

5. The method of claim 1, wherein said breast tissue is self-examined by said individual.

6. The method of claim 1, wherein said step of feeling said skin is performed while said individual is in a reclining position.

7. The method of claim 1, wherein said emulsion or gel composition is a gel composition.

8. The method of claim 1, wherein said aqueous dispersion medium comprises from about 10.5 to about 25 weight percent of a glycol.

9. The method of claim 8, wherein said ionic polymeric thickener is a carboxypolymethylene polymer, said cellulosic thickener is hydroxyethyl cellulose, and said glycol is propylene glycol.

10. The method of claim 9, wherein said gel composition comprises between about 1/10 of one weight percent and about three weight percent of said carboxypolymethylene polymer, from about 1/10 of one weight percent to about three weight percent of said hydroxyethyl cellulose, and between about 14 to about 22 weight percent of said propylene glycol.

11. The method of claim 10, wherein said gel composition comprises about ½ of one weight percent of said carboxypolymethylene polymer, about ¼ of one weight percent of said hydroxyethyl cellulose and about 18 weight percent of said propylene glycol.

* * * * *

UNITED STATES PATENT AND TRADEMARK OFFICE
CERTIFICATE OF CORRECTION

PATENT NO. : 5,873,367
DATED : Feb. 23, 1999
INVENTOR(S) : Buchalter

It is certified that error appears in the above-identified patent and that said Letters Patent is hereby corrected as shown below:

Column 1, line 5, after "1996" insert --.--

Column 1, line 6, delete "now abandoned".

Column 2, line 46, "ML" should read --mL--.

Signed and Sealed this

Twenty-seventh Day of July, 1999

Attest:

Q. TODD DICKINSON

*Attesting Officer*     *Acting Commissioner of Patents and Trademarks*